(12) United States Patent
Gunjima et al.

(10) Patent No.: US 6,562,259 B1
(45) Date of Patent: May 13, 2003

(54) ACRYLIC ACID DERIVATIVE COMPOUNDS AND POLYMERIC LIQUID CRYSTAL OBTAINED BY POLYMERIZING THE SAME

(75) Inventors: Tomoki Gunjima, Chikushino (JP); Mitsuru Kurosawa, Iwata (JP); Kouichi Murata, Yokohama (JP)

(73) Assignee: Asahi Glass Company, Limited, Tokyo (JP)

( * ) Notice: Subject to any disclaimer, the term of this patent is extended or adjusted under 35 U.S.C. 154(b) by 0 days.

(21) Appl. No.: 09/720,820

(22) PCT Filed: Jul. 13, 1999

(86) PCT No.: PCT/JP99/03780

§ 371 (c)(1), (2), (4) Date: Jan. 12, 2001

(87) PCT Pub. No.: WO00/03970

PCT Pub. Date: Jan. 27, 2000

(30) Foreign Application Priority Data

Jul. 14, 1998  (JP) ............................................. 10-199233

(51) Int. Cl.$^7$ ................................................ C09K 19/12
(52) U.S. Cl. .......................... 252/299.64; 428/1; 430/1; 252/582; 252/299.66
(58) Field of Search ...................... 428/1.1; 252/299.66, 252/299.6, 299.61, 299.62, 299.64, 299.65, 299.67

(56) References Cited

U.S. PATENT DOCUMENTS 6,180,028 B1 * 1/2001 Hotaka et al. ......... 252/299.66

2002/0060310 A1 * 5/2002 Hasebe et al. ......... 252/299.64

FOREIGN PATENT DOCUMENTS

EP          0 659 865    * 12/1994   ........... C09K/19/30

* cited by examiner

*Primary Examiner*—John A. McPherson
*Assistant Examiner*—Jennifer R. Sadula
(74) *Attorney, Agent, or Firm*—Oblon, Spivak, McClelland, Maier & Neustadt, P.C.

(57) ABSTRACT

The present invention provides a photopolymerizable liquid crystal monomer having high durability, a low melting point and an enantiotropic property.

The photopolymerizable liquid crystal monomer is a 4-(4-(alkyloxycarbonyloxy)benzoyloxy)phenyl acrylate represented by the following formula A [wherein Ph is a 1,4-phenylene group, and R is an alkyl group]:

$$CH_2=CHCOO-Ph-OCO-Ph-OCOO-R \qquad \text{Formula A}$$

Further, the present invention provides a polymer liquid crystal obtained by polymerizing a composition containing the monomer.

Further, the present invention provides an optical element employing the polymer liquid crystal, and an optical head employing the optical element as a polarizing hologram element.

21 Claims, 5 Drawing Sheets

ACRYLIC ACID DERIVATIVE COMPOUNDS AND POLYMERIC LIQUID CRYSTAL OBTAINED BY POLYMERIZING THE SAME

TECHNICAL FIELD

The present invention relates to an acrylic acid derivative compound and a polymer liquid crystal obtained by polymerizing it.

BACKGROUND ART

A photopolymerizable liquid crystal monomer having a photopolymerizable functional group imparted to a liquid crystal monomer, has both a nature as a monomer and a nature as a liquid crystal. Accordingly, when a photopolymerizable liquid crystal monomer is irradiated with light in an aligned state, it undergoes polymerization while maintaining the alignment, whereby a polymer having the alignment fixed will be obtained. The polymer liquid crystal thus obtained, has an optical anisotropy attributable to the refractive index anisotropy of the liquid crystal structure. Accordingly, a special characteristic can be imparted by controlling, the liquid crystal alignment state, and an application to a retardation film or to an optical head to be used for an optical head device, is expected.

The optical head device is a device whereby light from a light source is converged on an optical disk to write information on the optical disk, or reflected light from the optical disk is received by a light-receiving element to carry out reading out of the information from the optical disk. And, the optical head to be used for the device functions as a beam splitter.

Heretofore, the following is known as a diffraction grating to be used for an optical head. For example, there is one wherein an isotropic diffraction grating is formed in the shape of a rectangular grating (relief type) on glass or plastic by a dry etching method or by an injection molding method. As another example, there is one wherein an anisotropic diffraction grating is formed on the surface of crystal showing a refractive index anisotropy, which is combined with a quarter wave plate to provide polarization selectivity.

However, when used for an optical head, with an isotropic diffraction grating, utilization efficiency of going light (light heading to an optical disk from a light source) is about 50%, and utilization efficiency of returning light (light reflected by the optical disk and heading to a light-receiving element) is about 20%. Therefore, utilization efficiency of light in the round trip is about 10% at the maximum, and thus, there has been a problem that only low efficiency is obtainable.

On the other hand, with the method wherein an anisotropic diffraction grating is formed for the surface of a flat plate of crystal showing a refractive index anisotropy such as $LiNbO_3$ to provide polarization selectivity, thereby to obtain a high utilization efficiency of light in a round trip, the crystal having a refractive index anisotropy, itself, is expensive and can hardly be applicable to a consumer field. Further, as a method for forming a diffraction grating, a proton exchange method is common. However, in such a case, there has been a problem that protons in the proton exchange liquid are likely to diffuse into the $LiNbO_3$ substrate, whereby it has been difficult to form a grating with fine pitches.

When a photopolymerizable liquid crystal monomer is employed and after controlling the liquid crystal monomer alignment state, it is converted to a polymer liquid crystal, it is possible to obtain a high round trip efficiency equal to crystal showing a refractive index anisotropy. For example, a method may be mentioned wherein the polymer liquid crystal is filled in the grating to attain the high efficiency. Namely, in a liquid crystal cell, of which the surface of the substrate on one side is micro-processed to have a rectangular grating, the liquid crystal monomer is aligned usually so that the long axis direction of the liquid crystal monomer molecule is in parallel with the grating, whereupon the monomer is polymerized to form a polymer liquid crystal. At that time, the grating depth is optimized by adjusting the ordinary index of the polymer liquid crystal to be consistent with the refractive index of the grating substrate, whereby a high round trip efficiency can be obtained.

Theoretically, the diffraction efficiency will be maximum when $\lambda/2 = \Delta n \cdot d$ is satisfied, where d is the grating depth, $\Delta n$ is the refractive index anisotropy of the polymer liquid crystal, and $\lambda$ is the wavelength. And, it is possible to obtain a high level of light utilization efficiency such that the efficiency of ±primary diffracted light is about 40%, and the total efficiency is about 80%.

Since the material is inexpensive, the polymer liquid crystal can be applied to the consumer field and is expected to provide an excellent optical head. As the characteristics of such an optical head, it is required to have high durability and a high round trip efficiency with a fine pitch (at a level of at most 10 $\mu$m).

As a photopolymerizable liquid crystal monomer, a compound represented by the formula 2, 3 or 4 (in this specification, Ph represents an unsubstituted 1,4-phenylene group, and Cy represents an unsubstituted trans-1,4-cyclohexylene group) is, for example, known (Takatsu, Hasebe, The 106th Photopolymer Discussion Meeting Material, III-1).

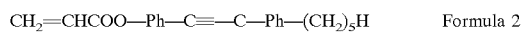

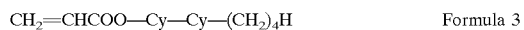

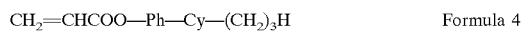

However, the compound represented by the formula 2 (hereinafter referred to also as compound 2, the same applies to other compounds) has a tolan group in its molecule and thus has had a problem that it lacks in durability. Whereas, compound 3 shows an enantiotropic nature, but the refractive index anisotropy of the monomer itself is low. And, compound 4 shows liquid crystal nature in the vicinity of room temperature, but it has had a problem that it is somewhat difficult to use, since it is a monotropic liquid crystal.

DISCLOSURE OF THE INVENTION

The present invention provides an acrylic acid derivative compound represented by the following formula 1 (hereinafter referred to also as compound 1) which is a photopolymerizable liquid crystal monomer having excellent durability and a low melting point $T_m$ and showing primarily an enantiotropic nature.

Further, the present invention provides a polymer liquid crystal obtained by polymerizing the above photopolymerizable liquid crystal monomer.

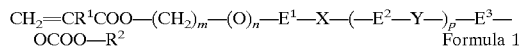

wherein the symbols have the following meanings:

$R^1$: a hydrogen atom or a methyl group, $R^2$: an alkyl group, $E^1$, $E^2$, $E^3$: each independently is a 1,4-phenylene group, wherein at least one hydrogen atom may be substituted by a fluorine atom, a chlorine atom or a methyl group, X, Y: each independently is a single bond or an oxycarbonyl group, m: an integer of from 0 to 8, n: 0 when m is 0, or 1 when m is at least 1, and p: 0 or 1.

BEST MODE FOR CARRYING OUT THE INVENTION

Figure 1:
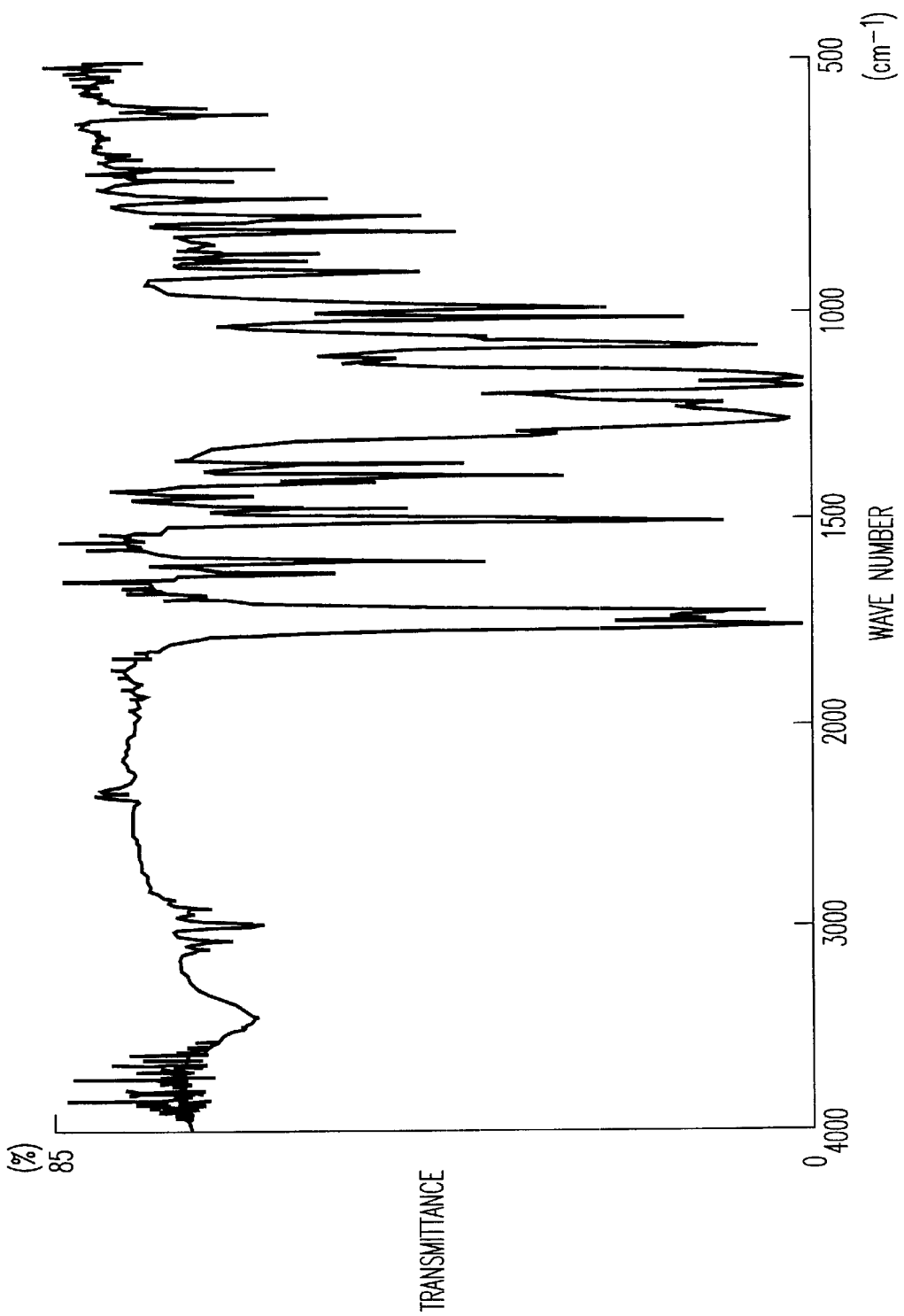
FIGS. 1 to 5 are infrared absorption spectra of compound 5A, compound 5B, compound 5C, compound 5D and compound 5E, respectively.

In compound 1, X and Y, each independently is a single bond or an oxycarbonyl group. Here, when X is an oxycarbonyl group, an oxy group in the oxycarbonyl group may be bonded to $E^1$, or a carbonyl group in the oxycarbonyl group may be bonded to $E^1$. Further, when Y is an oxycarbonyl group, an oxy group in the oxycarbonyl group may be bonded to $E^2$, or a carbonyl group in the oxycarbonyl group may be bonded to $E^2$.

As compound 1, a compound wherein $R^1$ is a hydrogen atom, each of $E^1$ and $E^3$ is an unsubstituted 1,4-phenylene group, X is an oxycarbonyl group (provided that the oxy group of the oxycarbonyl group is bonded to $E^1$), m is 0, and p is 0, is preferred. Namely, an acrylic acid derivative compound represented by the following formula 5, is preferred.

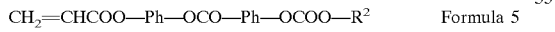

$$CH_2=CHCOO-Ph-OCO-Ph-OCOO-R^2 \quad \text{Formula 5}$$

In compound 1 and compound 5, if the carbon number of $R^2$ is too much, the melting point $T_m$ tends to be high. In order to maintain the melting point $T_m$ of the liquid crystal composition to a level of not higher than room temperature, $R^2$ is preferably a $C_{1-8}$ alkyl group. In such a case, $R^2$ is preferably a linear alkyl group, whereby the temperature range showing a liquid crystal nature will be wide.

Compound 5 can be prepared, for example, by the following method. Namely, hydroquinone and acrylic acid chloride are reacted to obtain 4-hydroxyphenyl acrylate (Formula 6) as a half ester. On the other hand, a 4-alkoxycarbonyloxy benzoic acid is heated and refluxed in a mixture of carbon-tetrachloride (a solvent) and thionyl chloride, and excess thionyl chloride and carbon tetrachloride (solvent) are distilled off under reduced pressure to obtain a 4-alkoxycarbonyloxy benzoic acid chloride (Formula 7). Then, in the presence of a base such as trimethylamine, the 4-hydroxyphenyl acrylate (Formula 6) and the 4-alkoxycarbonyloxy benzoic acid chloride (Formula 7) are reacted to obtain the compound 5.

$$CH_2=CHCOO-Ph-OH \quad \text{Formula 6}$$

$$ClCO-Ph-OCOO-R^2 \quad \text{Formula 7}$$

The physical properties of various compounds 5 which are different in the number of carbon atoms in $R^2$, are shown in Table 1. Here, $T_m$ represents the melting point (unit: °C.), and $T_c$ represents the nematic/isotropic phase transfer temperature (unit: °C.). All of compound 5A, compound 5B, compound 5C, compound 5D and compound 5E have been confirmed to be enantiotropic liquid crystals.

TABLE 1

|  | $R^2$ | $T_m$ | $T_c$ |
|---|---|---|---|
| Compound 5A | $(CH_2)_2H$ | 113 | 123 |
| Compound 5B | $(CH_2)_3H$ | 89 | 101 |
| Compound 5C | $(CH_2)_4H$ | 73 | 99 |
| Compound 5D | $(CH_2)_5H$ | 62 | 93 |
| Compound 5E | $(CH_2)_6H$ | 66 | 94 |

As acrylic acid derivative compounds represented by the Formula 1, the following compounds may be mentioned. $R^2$ is preferably a linear alkyl group.

$CH_2=CHCOO-Ph-OCO-Ph-OCOO-CH_3$, $CH_2=CHCOO-Ph-OCO-Ph-OCOO-C_2H_5$  Compound 5A $CH_2=CHCOO-Ph-OCO-Ph-OCOO-C_3H_7$  Compound 5B $CH_2=CHCOO-Ph-OCO-Ph-OCOO-C_4H_9$  Compound 5C $CH_2=CHCOO-Ph-OCO-Ph-OCOO-C_5H_{11}$  Compound 5D $CH_2=CHCOO-Ph-OCO-Ph-OCOO-C_6H_{13}$  Compound 5E $CH_2=CHCOO-Ph-OCO-Ph-OCOO-C_7H_{15}$, $CH_2=CHCOO-Ph-OCO-Ph-OCOO-C_8H_{17}$.

$CH_2=CHCOO-Ph-OCO-Ph-Ph-OCOO-CH_3$, $CH_2=CHCOO-Ph-OCO-Ph-Ph-OCOO-C_2H_5$, $CH_2=CHCOO-Ph-OCO-Ph-Ph-OCOO-C_3H_7$, $CH_2=CHCOO-Ph-OCO-Ph-Ph-OCOO-C_4H_9$, $CH_2=CHCOO-Ph-OCO-Ph-Ph-OCOO-C_5H_{11}$, $CH_2=CHCOO-Ph-OCO-Ph-Ph-OCOO-C_6H_{13}$, $CH_2=CHCOO-Ph-OCO-Ph-Ph-OCOO-C_7H_{15}$, $CH_2=CHCOO-Ph-OCO-Ph-Ph-OCOO-C_8H_{17}$.

$CH_2=CHCOO-CH_2-O-Ph-Ph-OCOO-CH_3$, $CH_2=CHCOO-CH_2-O-Ph-Ph-OCOO-C_2H_5$, $CH_2=CHCOO-CH_2-O-Ph-Ph-OCOO-C_3H_7$, $CH_2=CHCOO-CH_2-O-Ph-Ph-OCOO-C_4H_9$, $CH_2=CHCOO-CH_2-O-Ph-Ph-OCOO-C_5H_{11}$, $CH_2=CHCOO-CH_2-O-Ph-Ph-OCOO-C_6H_{13}$, $CH_2=CHCOO-CH_2-O-Ph-Ph-OCOO-C_7H_{15}$, $CH_2=CHCOO-CH_2-O-Ph-Ph-OCOO-C_8H_{17}$.

$CH_2=CHCOO-(CH_2)_2O-Ph-Ph-OCOO-CH_3$, $CH_2=CHCOO-(CH_2)_2O-Ph-Ph-OCOO-C_2H_5$, $CH_2=CHCOO-(CH_2)_2O-Ph-Ph-OCOO-C_3H_7$, $CH_2=CHCOO-(CH_2)_2O-Ph-Ph-OCOO-C_4H_9$, $CH_2=CHCOO-(CH_2)_2O-Ph-Ph-OCOO-C_5H_{11}$, $CH_2=CHCOO-(CH_2)_2O-Ph-Ph-OCOO-C_6H_{13}$, $CH_2=CHCOO-(CH_2)_2O-Ph-Ph-OCOO-C_7H_{15}$, $CH_2=CHCOO-(CH_2)_2O-Ph-Ph-OCOO-C_8H_{17}$.

$CH_2=CHCOO-(CH_2)_3O-Ph-Ph-OCOO-CH_3$, $CH_2=CHCOO-(CH_2)_3O-Ph-Ph-OCOO-C_2H_5$, $CH_2=CHCOO-(CH_2)_3O-Ph-Ph-OCOO-C_3H_7$, $CH_2=CHCOO-(CH_2)_3O-Ph-Ph-OCOO-C_4H_9$, $CH_2=CHCOO-(CH_2)_3O-Ph-Ph-OCOO-C_5H_{11}$, $CH_2=CHCOO-(CH_2)_3O-Ph-Ph-OCOO-C_6H_{13}$, $CH_2=CHCOO-(CH_2)_3O-Ph-Ph-OCOO-C_7H_{15}$, $CH_2=CHCOO-(CH_2)_3O-Ph-Ph-OCOO-C_8H_{17}$.

$CH_2=CHCOO-(CH_2)_4O-Ph-Ph-OCOO-CH_3$, $CH_2=CHCOO-(CH_2)_4O-Ph-Ph-OCOO-C_2H_5$, $CH_2=CHCOO-(CH_2)_4O-Ph-Ph-OCOO-C_3H_7$, $CH_2=CHCOO-(CH_2)_4O-Ph-Ph-OCOO-C_4H_9$, $CH_2=CHCOO-(CH_2)_4O-Ph-Ph-OCOO-C_5H_{11}$, $CH_2=CHCOO-(CH_2)_4O-Ph-Ph-OCOO-C_6H_{13}$, $CH_2=CHCOO-(CH_2)_4O-Ph-Ph-OCOO-C_7H_{15}$, $CH_2=CHCOO-(CH_2)_4O-Ph-Ph-OCOO-C_8H_{17}$.

$CH_2=CHCOO-(CH_2)_5O-Ph-Ph-OCOO-CH_3$, $CH_2=CHCOO-(CH_2)_5O-Ph-Ph-OCOO-C_2H_5$, $CH_2=CHCOO-(CH_2)_5O-Ph-Ph-OCOO-C_3H_7$, $CH_2=CHCOO-(CH_2)_5O-Ph-Ph-OCOO-C_4H_9$, $CH_2=CHCOO-(CH_2)_5O-Ph-Ph-OCOO-C_5H_{11}$, $CH_2=CHCOO-(CH_2)_5O-Ph-Ph-OCOO-C_6H_{13}$, $CH_2=CHCOO-(CH_2)_5O-Ph-Ph-OCOO-C_7H_{15}$, $CH_2=CHCOO-(CH_2)_5O-Ph-Ph-OCOO-C_8H_{17}$.

$CH_2=CHCOO-(CH_2)_6O-Ph-Ph-OCOO-CH_3$, $CH_2=CHCOO-(CH_2)_6O-Ph-Ph-OCOO-C_2H_5$, $CH_2=CHCOO-(CH_2)_6O-Ph-Ph-OCOO-C_3H_7$, $CH_2=CHCOO-(CH_2)_6O-Ph-Ph-OCOO-C_4H_9$, $CH_2=CHCOO-(CH_2)_6O-Ph-Ph-OCOO-C_5H_{11}$, $CH_2=CHCOO-(CH_2)_6O-Ph-Ph-OCOO-C_6H_{13}$, $CH_2=CHCOO-(CH_2)_6O-Ph-Ph-OCOO-C_7H_{15}$, $CH_2=CHCOO-(CH_2)_6O-Ph-Ph-OCOO-C_8H_{17}$.

$CH_2=CHCOO-(CH_2)_7O-Ph-Ph-OCOO-CH_3$, $CH_2=CHCOO-(CH_2)_7O-Ph-Ph-OCOO-C_2H_5$, $CH_2=CHCOO-(CH_2)_7O-Ph-Ph-OCOO-C_3H_7$, $CH_2=CHCOO-(CH_2)_7O-Ph-Ph-OCOO-C_4H_9$, $CH_2=CHCOO-(CH_2)_7O-Ph-Ph-OCOO-C_5H_{11}$, $CH_2=CHCOO-(CH_2)_7O-Ph-Ph-OCOO-C_6H_{13}$, $CH_2=CHCOO-(CH_2)_7O-Ph-Ph-OCOO-C_7H_{15}$, $CH_2=CHCOO-(CH_2)_7O-Ph-Ph-OCOO-C_8H_{17}$.

$CH_2=CHCOO-(CH_2)_8O-Ph-Ph-OCOO-CH_3$, $CH_2=CHCOO-(CH_2)_8O-Ph-Ph-OCOO-C_2H_5$, $CH_2=CHCOO-(CH_2)_8O-Ph-Ph-OCOO-C_3H_7$, $CH_2=CHCOO-(CH_2)_8O-Ph-Ph-OCOO-C_4H_9$, $CH_2=CHCOO-(CH_2)_8O-Ph-Ph-OCOO-C_5H_{11}$, $CH_2=CHCOO-(CH_2)_8O-Ph-Ph-OCOO-C_6H_{13}$, $CH_2=CHCOO-(CH_2)_8O-Ph-Ph-OCOO-C_7H_{15}$, $CH_2=CHCOO-(CH_2)_8O-Ph-Ph-OCOO-C_9H_{17}$.

$CH_2=CHCOO-CH_2-O-Ph-OCO-Ph-OCOO-CH_3$, $CH_2=CHCOO-CH_2-O-Ph-OCO-Ph-OCOO-C_2H_5$, $CH_2=CHCOO-CH_2-O-Ph-OCO-Ph-OCOO-C_3H_7$, $CH_2=CHCOO-CH_2-O-Ph-OCO-Ph-OCOO-C_4H_9$, $CH_2=CHCOO-CH_2-O-Ph-OCO-Ph-OCOO-C_5H_{11}$, $CH_2=CHCOO-CH_2-O-Ph-OCO-Ph-OCOO-C_6H_{13}$, $CH_2=CHCOO-CH_2-O-Ph-OCO-Ph-OCOO-C_7H_{15}$, $CH_2=CHCOO-CH_2-O-Ph-OCO-Ph-OCOO-C_8H_{17}$.

$CH_2=CHCOO-(CH_2)_2O-Ph-OCO-Ph-OCOO-CH_3$, $CH_2=CHCOO-(CH_2)_2O-Ph-OCO-Ph-OCOO-C_2H_5$, $CH_2=CHCOO-(CH_2)_2O-Ph-OCO-Ph-OCOO-C_3H_7$, $CH_2=CHCOO-(CH_2)_2O-Ph-OCO-Ph-OCOO-C_4H_9$, $CH_2=CHCOO-(CH_2)_2O-Ph-OCO-Ph-OCOO-C_5H_{11}$, $CH_2=CHCOO-(CH_2)_2O-Ph-OCO-Ph-OCOO-C_6H_{13}$, $CH_2=CHCOO-(CH_2)_2O-Ph-OCO-Ph-OCOO-C_7H_{15}$, $CH_2=CHCOO-(CH_2)_2O-Ph-OCO-Ph-OCOO-C_8H_{17}$.

$CH_2=CHCOO-(CH_2)_3O-Ph-OCO-Ph-OCOO-CH_3$, $CH_2=CHCOO-(CH_2)_3O-Ph-OCO-Ph-OCOO-C_2H_5$, $CH_2=CHCOO-(CH_2)_3O-Ph-OCO-Ph-OCOO-C_3H_7$, $CH_2=CHCOO-(CH_2)_3O-Ph-OCO-Ph-OCOO-C_4H_9$, $CH_2=CHCOO-(CH_2)_3O-Ph-OCO-Ph-OCOO-C_5H_{11}$, $CH_2=CHCOO-(CH_2)_3O-Ph-OCO-Ph-OCOO-C_6H_{13}$, $CH_2=CHCOO-(CH_2)_3O-Ph-OCO-Ph-OCOO-C_7H_{15}$, $CH_2=CHCOO-(CH_2)_3O-Ph-OCO-Ph-OCOO-C_8H_{17}$.

$CH_2=CHCOO-(CH_2)_4O-Ph-OCO-Ph-OCOO-CH_3$, $CH_2=CHCOO-(CH_2)_4O-Ph-OCO-Ph-OCOO-C_2H_5$, $CH_2=CHCOO-(CH_2)_4O-Ph-OCO-Ph-OCOO-C_3H_7$, $CH_2=CHCOO-(CH_2)_4O-Ph-OCO-Ph-OCOO-C_4H_9$, $CH_2=CHCOO-(CH_2)_4O-Ph-OCO-Ph-OCOO-C_5H_{11}$, $CH_2=CHCOO-(CH_2)_4O-Ph-OCO-Ph-OCOO-C_6H_{13}$, $CH_2=CHCOO-(CH_2)_4O-Ph-OCO-Ph-OCOO-C_7H_{15}$, $CH_2=CHCOO-(CH_2)_4O-Ph-OCO-Ph-OCOO-C_8H_{17}$.

$CH_2=CHCOO-(CH_2)_5O-Ph-OCO-Ph-OCOO-CH_3$, $CH_2=CHCOO-(CH_2)_5O-Ph-OCO-Ph-OCOO-C_2H_5$, $CH_2=CHCOO-(CH_2)_5O-Ph-OCO-Ph-OCOO-C_3H_7$, $CH_2=CHCOO-(CH_2)_5O-Ph-OCO-Ph-OCOO-C_4H_9$, $CH_2=CHCOO-(CH_2)_5O-Ph-OCO-Ph-OCOO-C_5H_{11}$, $CH_2=CHCOO-(CH_2)_5O-Ph-OCO-Ph-OCOO-C_6H_{13}$, $CH_2=CHCOO-(CH_2)_5O-Ph-OCO-Ph-OCOO-C_7H_{15}$, $CH_2=CHCOO-(CH_2)_5O-Ph-OCO-Ph-OCOO-C_8H_{17}$.

$CH_2=CHCOO-(CH_2)_6O-Ph-OCO-Ph-OCOO-CH_3$, $CH_2=CHCOO-(CH_2)_6O-Ph-OCO-Ph-OCOO-C_2H_5$, $CH_2=CHCOO-(CH_2)_6O-Ph-OCO-Ph-OCOO-C_3H_7$, $CH_2=CHCOO-(CH_2)_6O-Ph-OCO-Ph-OCOO-C_4H_9$, $CH_2=CHCOO-(CH_2)_6O-Ph-OCO-Ph-OCOO-C_5H_{11}$, $CH_2=CHCOO-(CH_2)_6O-Ph-OCO-Ph-OCOO-C_6H_{13}$, $CH_2=CHCOO-(CH_2)_6O-Ph-OCO-Ph-OCOO-C_7H_{15}$, $CH_2=CHCOO-(CH_2)_6O-Ph-OCO-Ph-OCOO-C_8H_{17}$.

$CH_2=CHCOO-(CH_2)_7O-Ph-OCO-Ph-OCOO-CH_3$, $CH_2=CHCOO-(CH_2)_7O-Ph-OCO-Ph-OCOO-C_2H_5$, $CH_2=CHCOO-(CH_2)_7O-Ph-OCO-Ph-OCOO-C_3H_7$, $CH_2=CHCOO-(CH_2)_7O-Ph-OCO-Ph-OCOO-C_4H_9$, $CH_2=CHCOO-(CH_2)_7O-Ph-OCO-Ph-OCOO-C_5H_{11}$, $CH_2=CHCOO-(CH_2)_7O-Ph-OCO-Ph-OCOO-C_6H_{13}$, $CH_2=CHCOO-(CH_2)_7O-Ph-OCO-Ph-OCOO-C_7H_{15}$, $CH_2=CHCOO-(CH_2)_7O-Ph-OCO-Ph-OCOO-C_8H_{17}$.

$CH_2=CHCOO-(CH_2)_8O-Ph-OCO-Ph-OCOO-CH_3$, $CH_2=CHCOO-(CH_2)_8O-Ph-OCO-Ph-OCOO-C_2H_5$, $CH_2=CHCOO-(CH_2)_8O-Ph-OCO-Ph-OCOO-C_3H_7$, $CH_2=CHCOO-(CH_2)_8O-Ph-OCO-Ph-OCOO-C_4H_9$, $CH_2=CHCOO-(CH_2)_8O-Ph-OCO-Ph-OCOO-C_5H_{11}$, $CH_2=CHCOO-(CH_2)_8O-Ph-OCO-Ph-OCOO-C_6H_{13}$, $CH_2=CHCOO-(CH_2)_8O-Ph-OCO-Ph-OCOO-C_7H_{15}$, $CH_2=CHCOO-(CH_2)_8O-Ph-OCO-Ph-OCOO-C_8H_{17}$.

$CH_2=CHCOO-CH_2-O-Ph-OCO-Ph-Ph-OCOO-CH_3$, $CH_2=CHCOO-CH_2-O-Ph-OCO-Ph-Ph-OCOO-C_2H_5$, $CH_2=CHCOO-CH_2-O-Ph-OCO-Ph-Ph-OCOO-C_3H_7$, $CH_2=CHCOO-CH_2-O-Ph-OCO-Ph-Ph-OCOO-C_4H_9$, $CH_2=CHCOO-CH_2-O-Ph-OCO-Ph-Ph-OCOO-C_5H_{11}$, $CH_2=CHCOO-CH_2-O-Ph-OCO-Ph-Ph-OCOO-C_6H_{13}$, $CH_2=CHCOO-CH_2-O-Ph-OCO-Ph-Ph-OCOO-C_7H_{15}$, $CH_2=CHCOO-CH_2-O-Ph-OCO-Ph-Ph-OCOO-C_8H_{17}$.

$CH_2=CHCOO-(CH_2)_2O-Ph-OCO-Ph-Ph-OCOO-CH_3$, $CH_2=CHCOO-(CH_2)_2O-Ph-OCO-Ph-Ph-OCOO-C_2H_5$, $CH_2=CHCOO-(CH_2)_2O-Ph-OCO-Ph-Ph-OCOO-C_3H_7$, $CH_2=CHCOO-(CH_2)_2O-Ph-OCO-Ph-Ph-OCOO-C_4H_9$, $CH_2=CHCOO-(CH_2)_2O-Ph-OCO-Ph-Ph-OCOO-C_5H_{11}$, $CH_2=CHCOO-(CH_2)_2O-Ph-OCO-Ph-Ph-OCOO-C_6H_{13}$, $CH_2=CHCOO-(CH_2)_2O-Ph-OCO-Ph-Ph-OCOO-C_7H_{15}$, $CH_2=CHCOO-(CH_2)_2O-Ph-OCO-Ph-Ph-OCOO-C_8H_{17}$.

$CH_2=CHCOO-(CH_2)_3O-Ph-OCO-Ph-Ph-OCOO-CH_3$, $CH_2=CHCOO-(CH_2)_3O-Ph-OCO-Ph-Ph-OCOO-C_2H_5$, $CH_2=CHCOO-(CH_2)_3O-Ph-OCO-Ph-Ph-OCOO-C_3H_7$, $CH_2=CHCOO-(CH_2)_3O-Ph-OCO-Ph-Ph-OCOO-C_4H_9$, $CH_2=CHCOO-(CH_2)_3O-Ph-OCO-Ph-Ph-OCOO-C_5H_{11}$, $CH_2=CHCOO-(CH_2)_3O-Ph-OCO-Ph-Ph-OCOO-C_6H_{13}$, $CH_2=CHCOO-(CH_2)_3O-Ph-OCO-Ph-Ph-OCOO-C_7H_{15}$, $CH_2=CHCOO-(CH_2)_3O-Ph-OCO-Ph-Ph-OCOO-C_8H_{17}$.

$CH_2=CHCOO-(CH_2)_4O-Ph-OCO-Ph-Ph-OCOO-CH_3$, $CH_2=CHCOO-(CH_2)_4O-Ph-OCO-Ph-Ph-OCOO-C_2H_5$, $CH_2=CHCOO-(CH_2)_4O-Ph-OCO-Ph-Ph-OCOO-C_3H_7$, $CH_2=CHCOO-(CH_2)_4O-Ph-OCO-Ph-Ph-OCOO-C_4H_9$, $CH_2=CHCOO-(CH_2)_4O-Ph-OCO-Ph-Ph-OCOO-C_5H_{11}$, $CH_2=CHCOO-(CH_2)_4O-Ph-OCO-Ph-Ph-OCOO-C_6H_{13}$, $CH_2=CHCOO-(CH_2)_4O-Ph-OCO-Ph-Ph-OCOO-C_7H_{15}$, $CH_2=CHCOO-(CH_2)_4O-Ph-OCO-Ph-Ph-OCOO-C_8H_{17}$.

$CH_2=CHCOO-(CH_2)_5O-Ph-OCO-Ph-Ph-OCOO-CH_3$, $CH_2=CHCOO-(CH_2)_5O-Ph-OCO-Ph-Ph-OCOO-C_2H_5$, $CH_2=CHCOO-(CH_2)_5O-Ph-OCO-Ph-Ph-OCOO-C_3H_7$, $CH_2=CHCOO-(CH_2)_5O-Ph-OCO-Ph-Ph-OCOO-C_4H_9$, $CH_2=CHCOO-(CH_2)_5O-Ph-OCO-Ph-Ph-OCOO-C_5H_{11}$, $CH_2=CHCOO-(CH_2)_5O-Ph-OCO-Ph-Ph-OCOO-C_6H_{13}$, $CH_2=CHCOO-(CH_2)_5O-Ph-OCO-Ph-Ph-OCOO-C_7H_{15}$, $CH_2=CHCOO-(CH_2)_5O-Ph-OCO-Ph-Ph-OCOO-C_8H_{17}$.

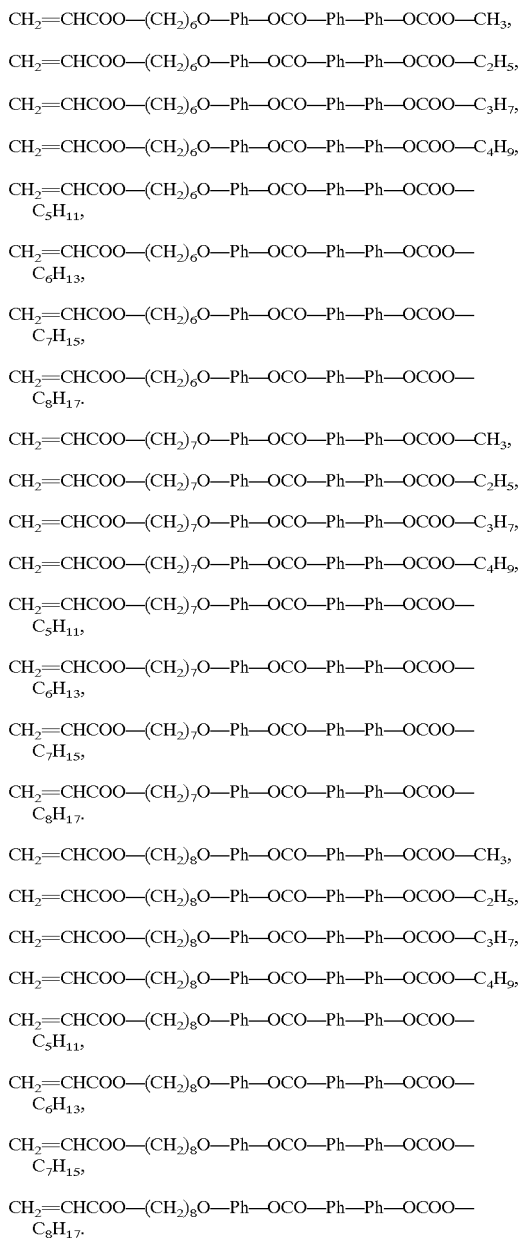

When used as a composition at least one type of compound 1 is preferably mixed with other polymerizable compound to obtain a composition having desired characteristics. The proportion of compound 1 in the composition is preferably at least 20 wt %, more preferably from 20 to 95 wt %, particularly preferably from 30 to 80 wt %.

In the composition to be used as a polymer liquid crystal, other liquid crystal compound may be incorporated. As such other liquid crystal compound, a component which shows liquid crystal nature at a low temperature, a low viscosity component for low temperature use, a component for improving the refractive index anisotropy, a component for improving the dielectric constant anisotropy or a component for imparting a cholesteric nature, may, for example, be mentioned, although it may vary depending upon the particular purpose or required performance.

Further, in the composition, other compound showing no liquid crystal nature may be incorporated, and the proportion of such other compound in the composition is preferably less than 50 wt %.

Using the composition thus prepared, photopolymerization is carried out to form a polymer liquid crystal.

When photopolymerization is to be carried out, a photopolymerization initiator may be employed, whereby polymerization can be carried out efficiently. Such photopolymerization initiator is not particularly limited, and acetophenones, benzophenones, benzoins, benzyls, Michler's ketones, benzoin alkyl ethers, benzyl dimethyl ketals, or thioxanthones, may, for example, be preferably employed. Further, two or more photopolymerizable initiators may be used in combination, as the case requires. The amount of the photopolymerization initiator is preferably from 0.1 to 10 wt %, particularly preferably from 0.5 to 2 wt %, based on the composition.

As light to be used for polymerization, ultraviolet rays or visible light may, for example, be mentioned. At that time, as a support, glass or plastic may, for example, be employed. Alignment treatment is applied to the support surface. The alignment treatment may be carried out by directly rubbing the support surface with e.g. natural fibers of e.g. cotton or wool, or with synthetic fibers of e.g. nylon or polyester, or by coating polyimide, polyamide or the like and then rubbing the coated surface with the above fibers or the like. A spacer such as glass beads, is disposed, so that a plurality of supports are controlled to face one another with desired distances, and between the supports, the above-mentioned composition is injected and filled.

In order to maintain the liquid crystal composition in the liquid crystal state, the temperature of the atmosphere is adjusted to be within a range of from $T_m$ to $T_c$. However, at a temperature close to $T_c$, the refractive index anisotropy tends to be very small. Accordingly, the upper limit of the temperature of the atmosphere is preferably set to be at most $(T_c-10)°$ C.

The polymer liquid crystal of the present invention may be used as it is sandwiched between supports, or may be employed after peeling it from the support.

The polymer liquid crystal thus prepared is suitable for an optical element. Specifically, it can be used as a retardation film. Further, a polarization hologram beam splitter having a high round trip efficiency and a polarization dependency, can be prepared by combining a polymer liquid crystal having the alignment controlled to be in the form of a grating, with a quarter wave plate, or by combining one having the polymer liquid crystal filled in grooves of a grating, with a quarter wave plate. And, using the same element, an optical head having a high light utilization efficiency can be prepared.

EXAMPLES

Example 1

Preparation of Compound 5C

While cooling a mixture comprising 110 g (1.0 mol) of hydroquinone, 800 ml of tetrahydrofuran and 106 g (1.05 mol) of triethylamine with ice water, 97 g (1.05 mol) of acrylic acid chloride was added thereto over a period of 3 hours. During the period, the reaction solution was vigorously stirred, and the temperature was maintained to be not higher than 20° C. It was left to stand with stirring for 12 hours, then filtration under reduced pressure was carried out, and the filtrate was concentrated under reduced pressure.

Then, to the concentrated solution, 350 ml of chloroform was added, and the mixture was cooled and left to stand, and then filtration under reduced pressure was carried out. To the filtrate, 150 ml of a 5% sodium hydrogen carbonate aqueous solution was added, and the organic layer was extracted. This operation was repeated four times, and 150 ml of 4% hydrochloric acid was added to extract the organic layer, and 150 ml of water was further added to extract the organic layer twice. Anhydrous magnesium sulfate was added thereto, and filtration under reduced pressure was carried out.

The filtrate was concentrated to 100 ml and then left to stand at room temperature overnight to precipitate crystals, and filtration under reduced pressure was carried out. The filtrate was concentrated under reduced pressure, and then 50 ml of dichloromethane was added, and column chromatography was carried out by developing dichloromethane in a column packed with basic alumina. After confirming the termination of elution of phenylene diacrylate, the basic alumina in the column was taken out, and 1 l of 10% hydrochloric acid and 1 l of dichloromethane were added thereto. After stirring, decantation was carried out.

After filtration under reduced pressure, the organic layer was extracted, washed with water and then dried by adding anhydrous magnesium sulfate. This filtrate was concentrated under reduced pressure to obtain 35 g of 4-hydroxyphenyl acrylate (Formula 6) (yield: 20%).

On the other hand, 15 ml of carbon tetrachloride (solvent) and 3 ml of thionyl chloride were added to 2.16 g (0.0158 mol) of 4-n-butoxycarbonyloxy benzoic acid, and the mixture was heated and refluxed. After sufficiently reacting them, excess thionyl chloride and carbon tetrachloride (solvent) were distilled off under reduced pressure to obtain 4-butoxycarbonyloxy benzoic acid chloride (one having Formula 7 wherein $R^2$ is a n-butyl group).

Then, a mixture comprising 15 ml of dry dichloromethane, 1.7 g (0.0165 mol) of triethylamine and 2.7 g (0.015 mol) of 4-butoxycarbonyloxy benzoic acid chloride, was cooled with ice water. Then, the above 4-hydroxyphenyl acrylate (compound 6) dissolved in 10 ml of dry dichloromethane, was added so that the temperature of the reaction solution did not exceed 10° C.

After reacting sufficiently with stirring, hydrochloric acid and water were added, and the organic layer was extracted and washed with water. Anhydrous magnesium sulfate was added thereto, and then filtration under reduced pressure was carried out to obtain powder crystal. Ethanol was added thereto for recrystallization. To this powder, hexane was added, and recrystallization was carried out again. Then, the obtained powder crystal was dissolved in 20 ml of dichloromethane, and column chromatography was carried out by developing dichloromethane in a column packed with silica gel. After confirming that there was no eluate, the extracted solution was purified to obtain 3.7 g (yield: 64%) of compound 5C i.e. 4-(4-butoxycarbonyloxy)benzoyloxy) phenyl acrylate.

Example 2

Preparation of Compounds 5A, 5B, 5D and 5E

In the same manner as in Example 1, the above-mentioned compound 5A i.e. 4-(4-ethoxycarbonyloxy)benzoyloxy) phenyl acrylate, compound 5B i.e. 4-(4-propoxycarbonyloxy)benzoyloxy)phenyl acrylate, compound 5D i.e. 4-(4-(pentyloxycarbonyloxy)benzoyloxy) phenyl acrylate, and compound 5E i.e. 4-(4-(hexyloxycarbonyloxy)benzoyloxy)phenyl acrylate, were obtained.

Example 3

Spectra of Compounds 5A, 5B, 5C, 5D and 5E

Figure 2:
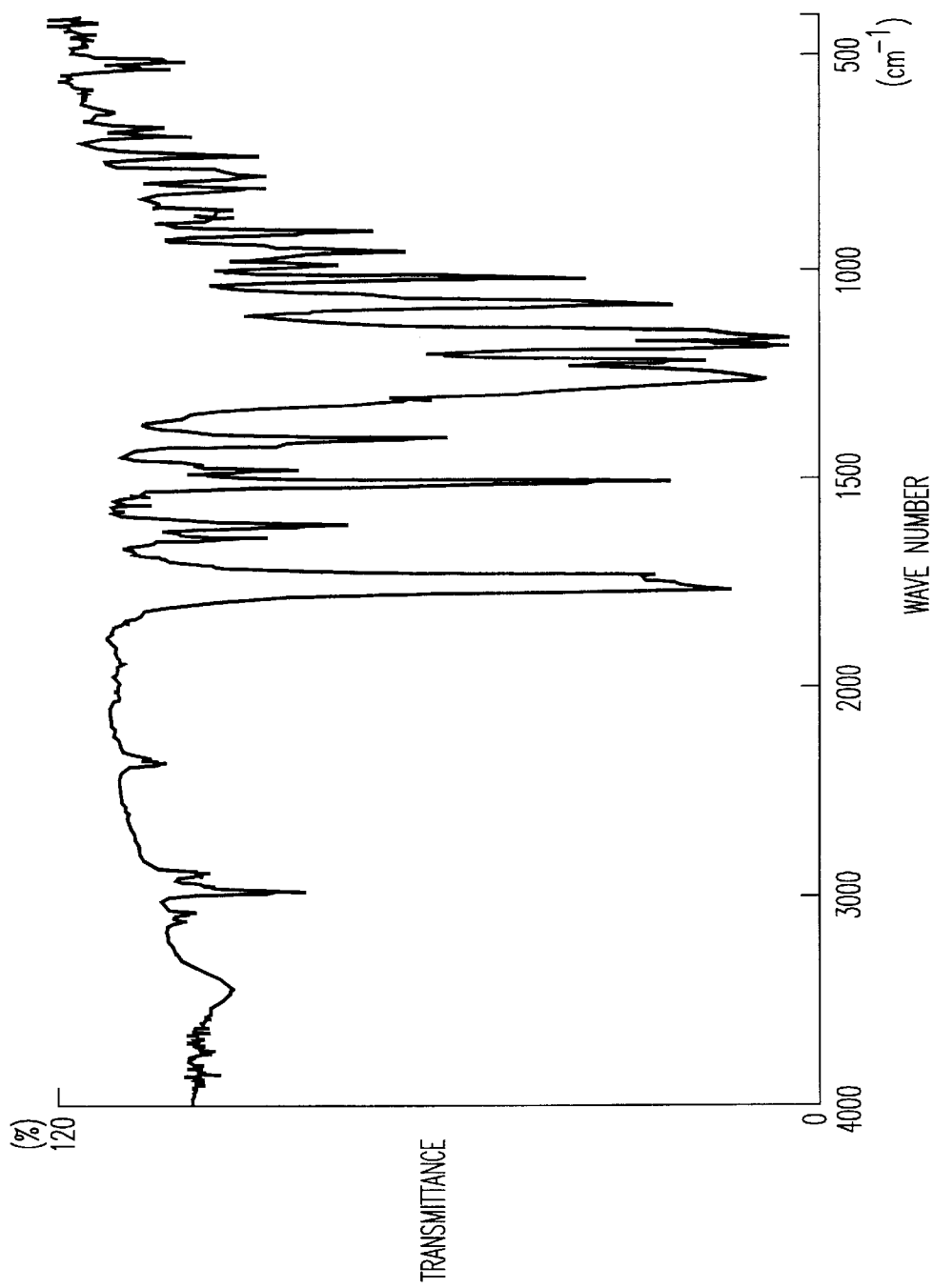
Figure 3:
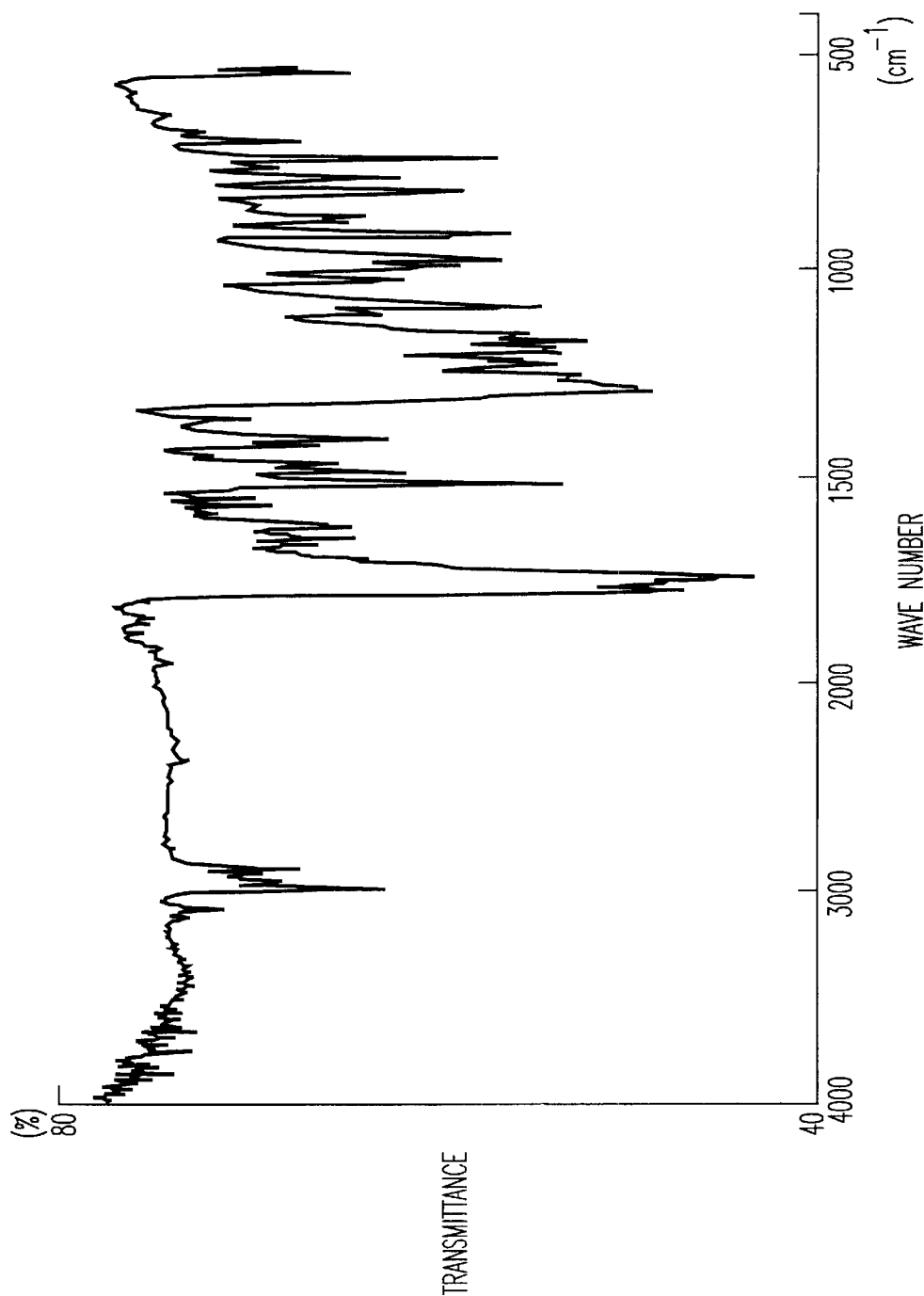
Figure 4:
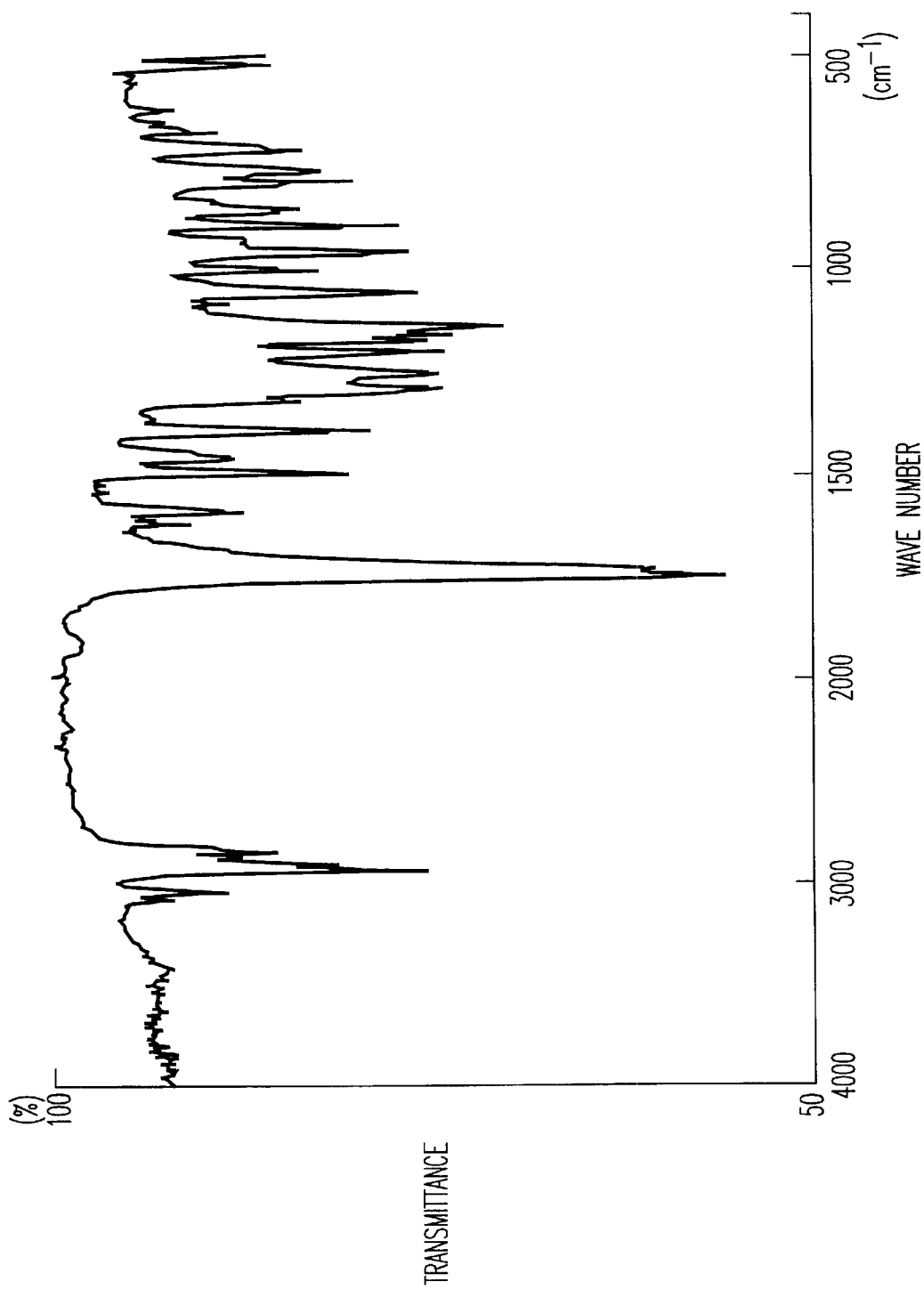
Figure 5:
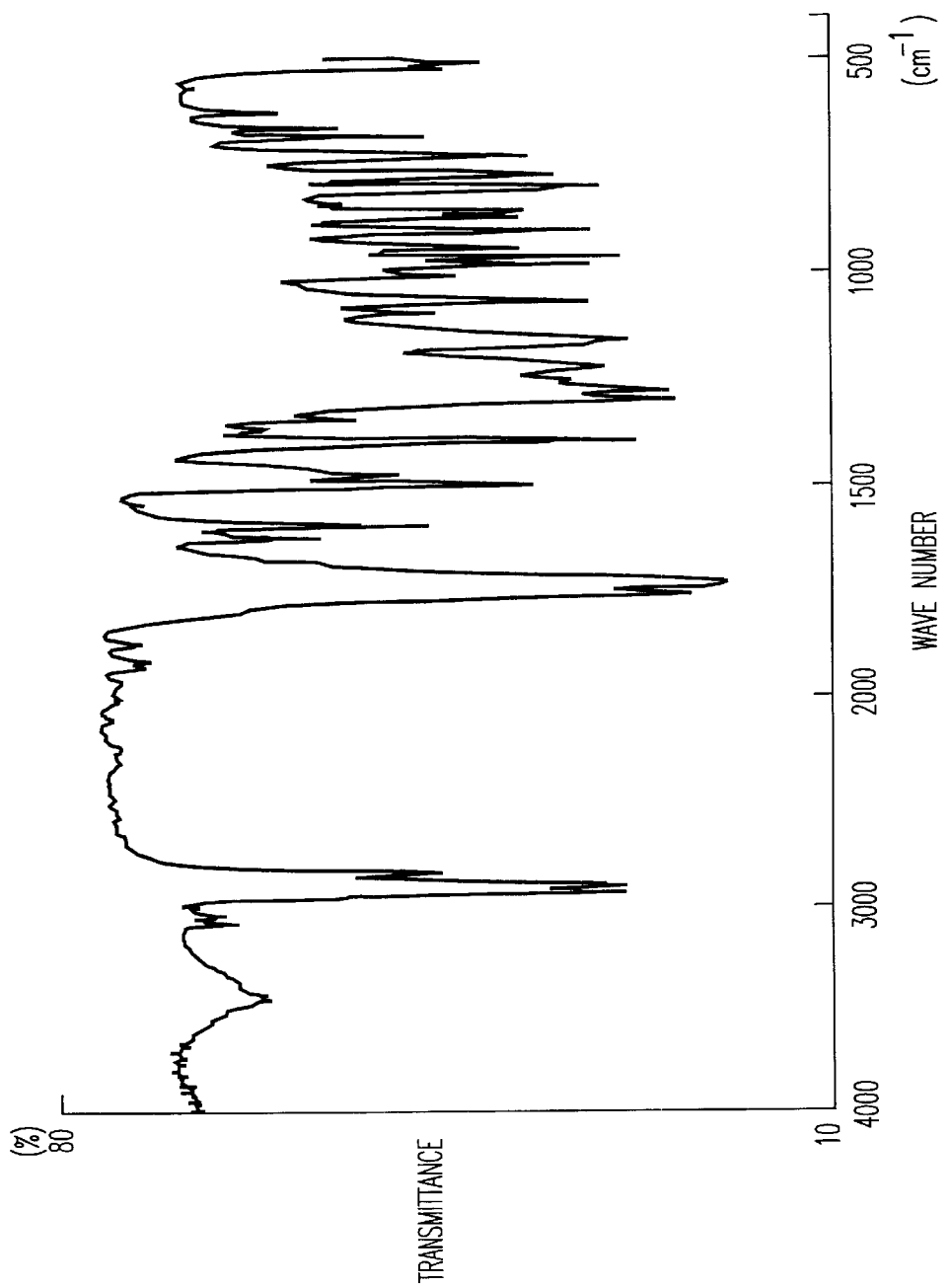

The infrared absorption spectrum (KBr tablet) of compound 5A is shown in FIG. 1; the infrared absorption spectrum (KBr tablet) of compound 5B is shown in FIG. 2; the infrared absorption spectrum (NaCl coating) of compound 5C is shown in FIG. 3; the infrared absorption spectrum (NaCl coating) of compound 5D is shown in FIG. 4; and the infrared absorption spectrum (NaCl coating) of compound 5E is shown in FIG. 5.

The 1H-NMR spectra (each with $CDCl_3$ solvent, TMS internal standard) of compound 5B, compound 5C, compound 5D and compound 5E, are shown, respectively, in Table 2.

TABLE 2

| Compound 5B δ (ppm) | | | |
|---|---|---|---|
| 0.8 to 2.0 | (complex | m | 7H) |
| 4.1 to 4.4 | (triplet | J = 6Hz | 2H) |
| 5.8 to 8.3 | (m | | 9H) |
| Compound 5C δ (ppm) | | | |
| 0.9 to 2.1 | (complex | m | 9H) |
| 4.1 to 4.4 | (triplet | J = 6Hz | 2H) |
| 5.8 to 8.3 | (m | | 9H) |
| Compound 5D δ (ppm) | | | |
| 0.4 to 2.0 | (complex | m | 11H) |
| 4.2 to 4.6 | (triplet | J = 6Hz | 2H) |
| 5.8 to 8.3 | (m | | 9H) |
| Compound 5E δ (ppm) | | | |
| 0.5 to 2.2 | (complex | m | 13H) |
| 4.2 to 4.75 | (triplet | J = 6Hz | 2H) |
| 5.8 to 8.4 | (m | | 9H) |

Example 4

Preparation of a Liquid Crystal Composition 22 wt % of compound 5D, 16 wt % of 4-(3-acryloyloxypropyl)oxy-4'-cyanobiphenyl (compound 8), 18 wt % of 4-(4-butylbenzoyloxy)phenyl acrylate (compound 9), 23 wt % of 4-(4-pentylbenzoyloxy)phenyl acrylate (compound 10) and 21 wt % of 4-(trans-4-pentylcyclohexylcarbonyloxy)phenyl acrylate (compound 11) were mixed to obtain a liquid crystal composition. This liquid crystal composition had $T_c$ of 74° C. and was a nematic liquid crystal at room temperature. The refractive index anisotropy was 0.15 at 589 nm at 25° C. The chemical formulae and physical properties of the compound 8, compound 9, compound 10 and compound 11 are shown in Table 3.

TABLE 3

|  |  | $T_m$ | $T_c$ |
|---|---|---|---|
| Compound 8 | $CH_2$=CHCOO$(CH_2)_3$OPhPhCN | 70 | 35 |
| Compound 9 | $CH_2$=CHCOOPhOCOPhC$_4$H$_9$ | 67 | 57 |
| Compound 10 | $CH_2$=CHCOOPhOCOPhC$_5$H$_{11}$ | 56 | 70 |
| Compound 11 | $CH_2$=CHCOOPhOCOCyC$_5$H$_{11}$ | 61 | 110 |

Example 5

Preparation of a Polymer Liquid Crystal

A glass plate having a polyimide as an alignment agent coated by a spin coater, followed by heat treatment and then having rubbing treatment applied in a predetermined direction by a nylon cloth, was used as a support. Two such support sheets were bonded by an adhesive so that the alignment-treated surfaces would face to each other to form a cell 1. At that time, glass beads were mixed to the adhesive and adjusted so that the distance between the supports would be 10 μm.

One having 0.5 wt % of a photopolymerization initiator "Irgacure 907 (manufactured by Ciba Geigy Company)" added to the liquid crystal composition of Example 4, was injected at 65° C. into the cell 1 prepared as described above. Then, ultraviolet rays with an intensity of 10 mW/cm² were irradiated at 20° C. for 300 seconds to carry out photopolymerization. After the polymerization, a polymer in a film form was obtained. This polymer was a polymer liquid crystal horizontally aligned in the rubbing direction of the substrates and having a refractive index anisotropy of 0.10 at 589 nm. This polymer liquid crystal was transparent in a visible light range, and no scattering was observed.

Example 6

Application to an Optical Head

A glass substrate having a rectangular grating with a pitch of 12 μm and a depth of 2 μm formed and having a polyimide as an alignment agent coated by a spin coater, followed by heat treatment and then subjected to rubbing treatment in a direction in parallel with the grating direction by a nylon cloth, and a glass flat plate substrate subjected to alignment treatment in the same manner, were bonded by means of an adhesive so that the respective alignment-treated surfaces would face each other, to prepare a cell 2. At that time, the alignment directions were adjusted to be parallel with each other.

One having 0.5 wt % of a photopolymerization initiator "Irgacure 907 (manufactured by Ciba Geigy Company)" added to a liquid crystal composition of Example 4, was injected at 65° C. into the cell 2 prepared as described above, to fill the grating recesses with the above composition. Then, ultraviolet rays with an intensity of 10 mW/cm² were irradiated for 300 seconds at 20° C. to carry out photopolymerization. On one side of this cell 2, a quarter wave plate was laminated to obtain a polarizing hologram beam splitter. This element was used for an optical head, a light utilization efficiency of 25% in total of efficiencies of ±primary diffraction grating was obtained by a laser light source with a wavelength of 650 nm.

Example 7

Preparation of a Liquid Crystal Composition 16.5 wt % of compound 5C, 16.5 wt % of compound 5D, 10 wt % of compound 8, 38 wt % of 4-(6-acryloyloxyhexyl)oxy-4'-cyanobiphenyl (compound 12) and 19 wt % of 4-acryloyloxy-4'-cyanobiphenyl (compound 13) were mixed to obtain a liquid crystal composition. This liquid crystal composition had $T_c$ of 79° C. and was a nematic liquid crystal at room temperature. The refractive index anisotropy was 0.21 at 589 nm at 25° C. The chemical formulae and physical properties of compound 12 and compound 13 are shown in Table 4.

TABLE 4

| | | $T_m$ | $T_c$ |
|---|---|---|---|
| Compound 12 | CH₂=CHCOO(CH₂)₆O-Ph-Ph-CN | 64 | 50 |
| Compound 13 | CH₂=CHCOO-Ph-Ph-CN | 102 | 129 |

INDUSTRIAL APPLICABILITY

According to the present invention, it is possible to prepare a photopolymerizable liquid crystal monomer which is a liquid crystal excellent in durability with low $T_m$ and showing mainly an enantiotropic nature. A liquid crystal composition employing it is a nematic liquid crystal at room temperature and has high $T_c$, whereby photopolymerization can be carried out at room temperature. A polymer liquid crystal obtained by the photopolymerization is useful for a retardation film or an optical head.

The present invention is applicable to various applications within a range not impair the effects of the present invention.

What is claimed is:

1. An acrylic acid derivative compound represented by the following formula 1:

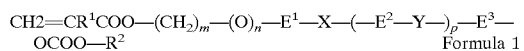

Formula 1 wherein the symbols have the following meanings:
$R^1$: a hydrogen atom or a methyl group,
$R^2$: an alkyl group,
$E^1$, $E^2$, $E^3$: each independently is a 1, 4phenylene group,
X, Y: each independently is a single bond or an oxycarbonyl group,
m: an integer of from 0 to 8,
n: 0 when m is 0, or 1 when m is at least 1, and
p: 0 or 1.

2. The acrylic acid derivative compound according to claim 1, wherein $R^2$ is a $C_{1-8}$ linear alkyl group.

3. The acrylic acid derivative compound according to claim 1, wherein at least one hydrogen atom of $E^1$, $E^2$, or $E^3$ may be substituted by a fluorine atom, a chlorine atom or a methyl group.

4. A composition containing at least 20 wt % of at least one acrylic acid derivative compound as defined in claim 1.

5. A polymer liquid crystal obtained by polymerizing the composition as defined in claim 4.

6. The polymer liquid crystal according to claim 5, obtained by the polymerization carried out by irradiating ultraviolet rays or visible light rays.

7. An optical element employing the polymer liquid crystal as defined in claim 5.

8. An optical head employing the optical element as defined in claim 7 as a polarizing hologram element.

9. The composition of claim 4, further comprising a photopolymerization initiator.

10. The composition of claim 9, wherein said a photopolymerization initiator is one or more photopolymerization initiators selected from the group consisting of a acetophenone, a benzophenone, a benzoin, a benzyl, a Michler's ketone, a benzoin alkyl ether, a benzyl dimethyl ketal, and a thioxanthone.

11. The acrylic acid derivative compound according to claim 1, wherein X is an oxycarbonyl group.

12. The acrylic acid derivative compound according to claim 11, wherein an carbonyl group in the oxycarbonyl group is bonded to $E^1$.

13. The acrylic acid derivative compound according to claim 11, wherein an oxy group in the oxycarbonyl group is bonded to $E^1$.

14. The acrylic acid derivative compound according to claim 1, wherein $R^1$ is a hydrogen atom, each of $E^1$ and $E^3$ is an unsubstituted 1,4—phenylene group, X is an oxycarbonyl group when the oxy group of the oxycarbonyl group is bonded to $E^1$, m is 0, and p is 0.

15. The acrylic acid derivative compound according to claim 14, wherein $R^2$ is a $C_{1-8}$ linear alkyl group.

16. The acrylic acid derivative compound according to claim 14, wherein said compound is represented by the following formula 5:

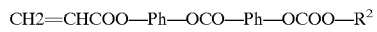

CH2=CHCOO—Ph—OCO—Ph—OCOO—R²      Formula 5 wherein $R^2$: an alkyl group.

17. A composition containing at least 20 wt % of at least one acrylic acid derivative compound as defined in claim 16.

18. The acrylic acid derivative compound according to claim 16, wherein $R^2$ is a $C_{1-8}$ linear alkyl group.

19. The acrylic acid derivative compound according to claim 1, wherein Y is an oxycarbonyl group.

20. The acrylic acid derivative compound according to claim 19, wherein an oxy group in the oxycarbonyl group is bonded to $E^2$.

21. The acrylic acid derivative compound according to claim 19, wherein an carbonyl group in the oxycarbonyl group is bonded to $E^2$.

\* \* \* \* \*